United States Patent [19]

Halbritter et al.

[11] Patent Number: 4,891,435
[45] Date of Patent: Jan. 2, 1990

[54] PREPARATION OF 4,4-DIMETHYLTETRAHYDROFURAN-2,3-DIONE

[75] Inventors: Klaus Halbritter, Mannheim; Manfred Eggersdorfer, Gruenstadt, both of Fed. Rep. of Germany

[73] Assignee: BASF Aktiengesellschaft, Ludwigshafen, Fed. Rep. of Germany

[21] Appl. No.: 719,332

[22] Filed: Apr. 3, 1985

Related U.S. Application Data

[63] Continuation of Ser. No. 519,093, Aug. 1, 1983, abandoned.

[30] Foreign Application Priority Data

Aug. 4, 1982 [DE] Fed. Rep. of Germany ....... 3229026

[51] Int. Cl.⁴ ............................................. C07D 307/08
[52] U.S. Cl. ...................................................... 549/313
[58] Field of Search ......................................... 549/313

[56] References Cited

U.S. PATENT DOCUMENTS 2,712,553 7/1955 Feltzin ................................ 549/313
3,474,112 10/1969 Galantay ............................ 549/313

FOREIGN PATENT DOCUMENTS 0006156 1/1980 European Pat. Off. .
0050721 5/1982 European Pat. Off. ............ 549/313

OTHER PUBLICATIONS

R. Kuhn et al, Berichte 75(2) (1942) pp. 121–122.
S. H. Lipton et al, Chemical Society Journal (London) vol. 71 (1949) pp. 2364–2367.
J. S. Little, Chemical Society Journal (London) (1954) pp. 2636–2637.
M. Tichy et al, Chemical Abstracts, vol. 50 (1956) 8532i.
Labib et al, Compt. Rend. (1960) vol. 250, pp. 2904–2905.
Houben-Weyl, vol. VI/2 (1963) pp. 571–572, 631–632.

*Primary Examiner*—Glennon H. Hollrah
*Assistant Examiner*—Amelia A. Owens
*Attorney, Agent, or Firm*—John H. Shurtleff

[57] ABSTRACT

4,4-Dimethyltetrahydrofuran-2,3-dione is prepared by reacting a dimethylpyruvate (II) with formaldehyde or a formaldehyde donor at 80°–150° C.

15 Claims, No Drawings

PREPARATION OF 4,4-DIMETHYLTETRAHYDROFURAN-2,3-DIONE

This application is a continuation of application Ser. No. 519,093, filed Aug. 1, 1983, now abandoned.

The present invention relates to a novel process for the preparation of 4,4-dimethyltetrahydrofuran-2,3-dione (I)

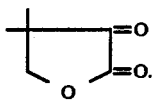   I

This compound, which is also referred to as α-ketopantolactone or 4,4-dimethyldihydrofuran-2,3-dione, is an important intermediate for the preparation of D-(-)-pantolactone (4,4-dimethyl-2-hydroxybutyrolactone) by asymmetric hydrogenation.

The paper by Kuhn and Wieland in Chem. Ber. 75 (1942), 121 discloses that dimethylpyruvic acid and formaldehyde in aqueous solution can be converted by means of potassium carbonate to 3,3-dimethyl-2-oxo-4-hydroxybutyric acid, which can then be lactonized, in a medium containing hydrochloric acid, to give the compound I. The yield obtained in this procedure was 60%, but, according to Lipton and Strong, J. Amer. Chem. Soc. 71 (1949), 2364, it is not certain whether the product is actually I.

The lastmentioned authors have therefore prepared I by a different route, ie. by oxidation of pantolactone with lead tetraacetate, but they obtained a yield of only 33%.

Improvement of the oxidation process finally led to yields of 70–90% when alkali metal or alkaline earth metal hypochlorites were used as oxidizing agents (EP-A1 0,006,156), but this method is unsatisfactory because the reaction mixture is heterogeneous and gives rise to technical difficulties in the working up procedure.

It is an object of the present invention to prepare the title compound in a simpler and mole economical manner.

We have found that this object is achieved, and that 4,4-dimethyltetrahydrofuran-2,3-dione (I) can be prepared by a process wherein a dimethylpyruvate (II) is reacted with formaldehyde or a formaldehyde donor at 80°–150° C.

This process is remarkable because, contrary to all expectations, it gives yields of 80–90%, based on II, by a smooth reaction.

On the basis of observations to date, the choice of the alcohol radical in the starting ester II is in principle not critical, and II may therefore be derived from an aliphatic, cycloaliphatic, araliphatic or aromatic alcohol. For practical reasons, however, preferred esters are those of alkanols of 1 to 8, preferably 1 to 4, carbon atoms, in particular the ester with methanol, ethanol, isopropanol, isobutanol or tert.butanol.

Although the reaction velocity decreases as the molecular weight of the alcohol increases, this effect is not so important as to render the process unattractive, especially since it can be substantially compensated by choosing harsher reaction conditions. Hence, for example, it is also possible to use the ester of cyclohexanol, of benzyl alcohol or of phenol as a starting compound.

The dimethylpyruvates II in turn are obtainable in high yields by reacting isobutyraldehyde with hydrocyanic acid and the appropriate alcohol and then subjecting the product to oxidative dehydroge-nation.

The formaldehyde can be used in the form of an aqueous or organic solution or as a gas, or a formaldehyde donor, eg. paraformaldehyde, can be employed. Since the formaldehyde has reducing properties and is capable of effecting the undesirable hydrogenation of the 3-keto group of I or II, it is advantageously employed in not too large an excess, but in an amount such that the ratio of formaldehyde to ester II is from about 1.0:1 to about 1.3:1.

In principle, the reaction can be carried out in the absence of a solvent, for example by passing gaseous formaldehyde into the liquid ester II, or by allowing paraformaldehyde to react with II with the addition of a little acid. For technical reasons, however, it is advisable to carry out the reaction in the presence of a solvent or diluent in the heterogeneous or, preferably, homogeneous phase.

Examples of suitable solvents and diluents are water and particularly organic solvents, especially $C_6$-$C_{12}$-hydrocarbons and $C_1$-$C_4$-alkanols, ethers, such as diethyl ether, ketones, such as acetone, chlorohydrocarbons and mixtures of these liquids. It is particularly advantageous if the formaldehyde is employed in the form of its solutions in the organic solvents, particularly in the $C_1$-$C_4$-alkanols. In general, the amount of solvent or diluent is from 0.5 to 20 liters per kg of II. Larger amounts have no adverse effects but do of course result in a more expensive working Op procedure.

The process proceeds very satisfactorily even in the absence of catalytically active substances; however, the concomitant use of an acidic or basic catalyst is advantageous, permitting a reduction in the reaction temperatures and/or the reaction times.

Suitable catalysts are inorganic acids, eg. sulfuric acid, hyrochloric acid and sodium hydrogen sulfate, organic acids, eg. formic acid and acetic acid, inorganic bases, eg. sodium hydroxide, sodium carbonate and sodium methylate and the corresponding potassium compounds, and organic bases, such as tertiary nitrogen bases, eg. trimethylamine and triethylamine. The effective amount of these catalysts is in general from 0.01 to 1% by weight of II. Larger amounts are possible, but as a rule hardly have any economic advantages.

At below 80° C., the reaction is so slow as to be uneconomical, while at above 150° C. side-reactions are increasingly noticeable. The reaction is preferably carried out at 100°–150° C., in particular 130°–145° C. If a catalyst is present, the temperature can be reduced by about 10°–20° C. for the same reaction times. Conversely, in the presence of a catalyst the reaction time can be Virtually halved for the same temperature.

The reaction is carried out under the autogenous pressure associated with the reaction temperature used; this pressure is about 1–4 bar.

In contrast to the procedure described by Kuhn and Wieland (loc. cit.), formaldehyde addition and ring closure take place virtually simultaneously, so that no 3,3-dimethyl-2-oxo-4-hydroxybutyrate is detectable in the reaction mixture. This is particularly advantageous because it permits one step, ie. separate lactonization, to be dispensed with.

The reaction times for virtually quantitative conversion of II are as a rule 2–5 hours, depending on the reaction conditions.

Otherwise, the process can be carried out using a conventional batchwise or continuous technique. This also applies to the working up of the reaction mixture, which is preferably carried out by distillation. However, if I is to be reacted further, it may not be necessary to isolate it.

EXAMPLE 1

68.8 g (0.4 mole) of isobutyl dimethylpyruvate and a solution of 24 g of isobutanol and 12 g of formaldehyde (0.4 mole of $CH_2O$) were heated at 110° C. for 2 hours in a stirred autoclave of 250 ml capacity. Working up the reaction mixture by a conventional distillation procedure gave pure δ-ketopantolactone in 89% yield. Bp. 85°-90° C./2 mbar, mp. 68°-70° C.

EXAMPLE 2

Reaction of 58 g (0.4 mole) of ethyl dimethylpyruvate with 44 g of a 30% strength by weight aqueous formaldehyde solution (0.44 mole of $CH_2O$) at 145° C. for 3 hours followed by extraction of I by means of diethyl ether and distillation of the extract gave the pure product in 83% yield.

EXAMPLE 3

The procedure was carried out similarly to that described in Example 2, except that in addition 0.4 g of triethylamine was used as a catalyst, the reaction temperature was 135° C. and the reaction time was 2.5 hours. The product was obtained in 87% yield.

EXAMPLE 4

The procedure was carried out similarly to that described in Example 2, except that in addition 0.3 g of sulfuric acid was used as a catalyst, the reaction temperature was 140° C. and the reaction time was 2 hours. The product was obtained in 83% yield.

We claim:

1. A process for the preparation of 4,4-dimethyltetrahydrofuran-2,3-dione which comprises reacting an alkanol ester of dimethylpyruvic acid, said alkanol containing 1 to 8 carbon atoms, with formaldehyde or paraformaldehyde as a formaldehyde donor at a temperature of 80°-150° C.

2. A process as claimed in claim 1 wherein the alkanol contains 1 to 4 carbon atoms.

3. A process as claimed in claim 1 wherein the ester reactant is isobutyl dimethylpyruvate.

4. A process as claimed in claim 1 wherein the ester reactant is ethyl dimethylpyruvate.

5. A process as claimed in claim 1 wherein the reaction is carried out in an aqueous solution of formaldehyde.

6. A process as claimed in claim 1 wherein the reaction is carried out in an organic solvent as the reaction medium for the formaldehyde and ester reactants.

7. A process as claimed in claim 6 wherein the organic solvent is selected from the group consisting of $C_6$- to $C_{12}$-hydrocarbons, $C_1$- to $C_4$-alkanols, ethers, ketones and chlorohydrocarbons.

8. A process as claimed in claim 1 wherein the reaction is carried out in a $C_1$- to $C_4$-alkanol as a solvent medium.

9. A process as claimed in claim 1 wherein the reaction is carried out in the presence of a catalytic amount of an acidic or basic catalyst.

10. A process as claimed in claim 1 using a reaction temperature of 100°-150° C.

11. a process as claimed in claim 1 using a molar ratio of the formaldehyde to the ester of from about 1.0:1 to about 1.3:1.

12. A process as claimed in claim 11 using a reaction temperature of 100°-150° C.

13. A process as claimed in claim 12 using a reaction temperature of 130°-145° C.

14. A process as claimed in claim 12 wherein the reaction is carried out in the homogenous phase using an organic solvent as the reaction medium for the formaldehyde and ester reactants.

15. A process as claimed in claim 12 wherein the reaction is carried out in a $C_1$- to $C_4$-alkanol as a solvent medium.

* * * * *